(12) United States Patent
Campisi

(10) Patent No.: US 10,660,510 B2
(45) Date of Patent: May 26, 2020

(54) LIPOSUCTION CANNULA WITH IMAGING MEANS

(71) Applicant: Corrado Campisi, Genoa (IT)

(72) Inventor: Corrado Campisi, Genoa (IT)

( * ) Notice: Subject to any disclaimer, the term of this patent is extended or adjusted under 35 U.S.C. 154(b) by 418 days.

(21) Appl. No.: 15/540,680

(22) PCT Filed: Dec. 23, 2015

(86) PCT No.: PCT/IB2015/059932
§ 371 (c)(1),
(2) Date: Jun. 29, 2017

(87) PCT Pub. No.: WO2016/108153
PCT Pub. Date: Jul. 7, 2016

(65) Prior Publication Data
US 2018/0000331 A1    Jan. 4, 2018

(30) Foreign Application Priority Data

Dec. 29, 2014    (IT) .............................. TO2014A1113

(51) Int. Cl.
*A61B 1/05*    (2006.01)
*A61B 17/22*    (2006.01)
(Continued)

(52) U.S. Cl.
CPC ............ *A61B 1/05* (2013.01); *A61B 1/00172* (2013.01); *A61B 17/22* (2013.01); *A61B 90/37* (2016.02);
(Continued)

(58) Field of Classification Search
CPC ....... A61B 1/05; A61B 1/00172; A61B 1/012; A61B 17/22; A61B 5/0059; A61B 5/6846;
(Continued)

(56) References Cited

U.S. PATENT DOCUMENTS

| | | | |
|---|---|---|---|
| 5,242,386 A | 9/1993 | Holzer | |
| 2010/0241058 A1* | 9/2010 | Ahmed | A61B 5/0066 604/20 |
| 2011/0257661 A1* | 10/2011 | Choi | A61B 1/00094 606/130 |

FOREIGN PATENT DOCUMENTS

WO    2007/134370 A1    11/2007

OTHER PUBLICATIONS

Eric J. Seibel et al. "A full-color scanning fiber endoscope" Optical Fibers and Sensors for Medical Diagnostics and Treatment Applications VI vol. 6083, 608303, (2006).
(Continued)

*Primary Examiner* — Phillip R Weist
(74) *Attorney, Agent, or Firm* — Arent Fox LLP; Michael Fainberg

(57) ABSTRACT

Disclosed herein a liposuction cannula that comprises a tube with a front end at which there is provided at least one suction opening, and with a back end intended to be connected to a source of vacuum; in the tube there being defined at least one longitudinal flow conduit for the aspirated material; and an imaging apparatus capable of supplying first signals or data allowing the generation of a visual representation of the environment in close proximity to the front end of the tube of the cannula down to a first depth or distance, and second signals or data allowing the generation of a visual representation of the environment around the front end of the tube of the cannula down to a second depth or distance, greater than the said first depth or distance.

8 Claims, 5 Drawing Sheets

(51) Int. Cl.
- *A61B 90/00* (2016.01)
- *A61B 1/00* (2006.01)
- *A61B 17/00* (2006.01)
- *A61B 1/012* (2006.01)
- *A61B 90/30* (2016.01)
- *A61B 5/00* (2006.01)
- *A61B 17/3207* (2006.01)
- *A61M 1/00* (2006.01)

(52) U.S. Cl.
CPC ............ *A61B 1/012* (2013.01); *A61B 5/0059* (2013.01); *A61B 5/6846* (2013.01); *A61B 17/320708* (2013.01); *A61B 2017/00022* (2013.01); *A61B 2017/00792* (2013.01); *A61B 2017/22079* (2013.01); *A61B 2090/306* (2016.02); *A61B 2090/3614* (2016.02); *A61B 2090/3735* (2016.02); *A61B 2090/3784* (2016.02); *A61B 2090/3941* (2016.02); *A61B 2217/005* (2013.01); *A61M 1/008* (2013.01); *A61M 2202/08* (2013.01)

(58) Field of Classification Search
CPC ............ A61B 17/320708; A61B 90/37; A61B 2090/306; A61B 2090/3614; A61B 2090/3735; A61B 2090/3784; A61B 2090/3941

See application file for complete search history.

(56) References Cited

OTHER PUBLICATIONS

Cameron M. Lee et al. "Scanning fiber endoscopy with highly flexible, 1-mm catheterscopes for wide-field, full-color imaging" J Biophotonics. Jun. 2010; 3(5-6): 385-407.

Wei-Cheng Kuo, "Real-time three-dimensional optical coherence tomography image-guided core-needle biopsy system", Jun. 1, 2012 / vol. 3, No. 6 / Biomedical Optics Express 1149.

Douglas N. Stephens et al. "First In Vivo Use of a Capacitive Micromachined Ultrasound Transducer Array-Based Imaging and Ablation Catheter" American Institute of Ultrasound in Medicine | J Ultrasound Med 2012; 31:247-256.

D. Lorenser et al. "Ultrathin side-viewing needle probe for optical coherence tomography" Optics Letters / vol. 36, No. 19 / Oct. 1, 2011.

International Search Report for PCT/IB2015/059932 dated Mar. 29, 2016.

* cited by examiner

LIPOSUCTION CANNULA WITH IMAGING MEANS

CROSS-REFERENCE TO RELATED APPLICATIONS

This application is a National Stage entry of International Application No. PCT/IB2015/059932 filed on Dec. 23, 2015, which claims priority to Italian Patent Application No. TO2014A001113 filed on Dec. 29, 2014. the entire contents of which is hereby incorporated in its entirety by reference.

The present invention relates to a liposuction cannula.

More specifically, the subject of the invention is a liposuction cannula of the type comprising a tube with a closed front end at which is formed at least one suction opening and with an open back end intended to be connected to a source of vacuum, in the tube there being defined at least one longitudinal flow conduit for the aspirated material, and detector means arranged at the front end of said tube and capable of providing in use signals containing information useful for the operator using the cannula.

DESCRIPTION OF THE PRIOR ART

Liposuction is a technique which has been developed by plastic surgeons for the removal, for aesthetic purposes, of excess body fat by means of a cannula, for example made of metal or plastic material, introduced under the epidermis and connected to a source of vacuum.

The liposuction initially consisted in the dry insertion of a thin cannula under the epidermis through a small incision and in the aspiration of the fatty tissue.

The more recent techniques provide the ablation of the fatty tissue with the aid of vibrations (PAL—Power Assisted Liposuction), ultrasound (UAL—Ultrasound Assisted Liposuction), or laser (LAL—Laser Assisted Liposuction) which help to remove the fibrotic tissue and to reduce the intervention times.

The initial technique of dry liposuction, because of the excessive loss of blood, was very early on replaced with the "tumescent" technique, in which adrenaline, lidocaine and a physiological solution are injected into the tissues prior to initiating the intervention, in order to avoid excessive bleeding.

Although the tumescent technique has allowed the complications associated with the blood losses to be reduced, there however remains the risk associated with the other serious side-effects, the most worrying of which is damage to the adjacent tissues, resulting from an inadequate technique of use of the cannula and the conditions of low visibility.

In particular, the most recent liposuction techniques (PAL and UAL) make the occurrence of unintentional perforations of the adjacent structures easier. In some cases, the perforation of abdominal organs has occurred as a result of the incorrect positioning of the cannula.

Equally worrying is the recent development and use of ultrathin cannulae which allow a more superficial use and with which significant tissue necroses are associated, owing to damage caused by the cannula to the superficial vascular network.

Although liposuction is a medical procedure principally developed for aesthetic ends, in the past few years, it has also been used for the treatment of some pathologies, amongst which are lymphoedema and lipoedema, associated with an increase in the fatty and fibrotic tissue in the affected limbs.

In lymphoedema, the accumulation of fatty tissue accompanies the progression of the disease and is correlated with a situation of chronic lymphostasis which, aside from the detrimental effects that this causes in the affected parts of the body, can lead to serious complications, including serious and chronic infections. For these reasons, in the past, such excess tissues were surgically removed, even if the results of such interventions for "de-bulking" were anything but satisfactory and often associated with poor healing of the wounds and with ugly resulting scars.

Recently, liposuction with assisted aspiration has been introduced as a less invasive procedure for removing the excess fatty tissues. In view of the already low lymphatic drainage in the patients in question, it is becoming increasingly necessary to pay attention to avoiding further damaging the lymphatic vessels during liposuction. In patients with lymphoedema, the lymphatic vessels and channels are often dilated and tortuous, in particular in the advanced stages of the disease, or else when liposuction is prescribed, and thus they can be more difficult to avoid with the cannula and more vulnerable to lesions.

Furthermore, the application of liposuction to pathologies such as lipoedema and lymphoedema also requires the treatment of the calves and of the lower part of the leg, areas that are not usually treated in the applications with aesthetic goals, which are limited in most cases to the thighs and to the abdomen. The calves have only one layer of subcutaneous fat, being less dense and easier to suck out with the aspiration, which renders the surface layer more vulnerable to accidental damage caused by the cannula, with a higher risk of complications and infections.

In order to at least partially overcome the aforementioned problems and drawbacks, the use of an external echograph to supply images able to guide the insertion and the movement of the cannula during the liposuction may, at least in theory, be considered. However, with this, a further instrument would be introduced into the sterile surgical area, which would increase the potential risk of contamination. Furthermore, from a practical point of view, the use of an ultrasound echograph at the same time as using a liposuction cannula would be problematic.

As an alternative, periodically introducing a thin endoscope into the channel created by the liposuction cannula inside the fatty tissue may be considered. This, however, requires both the endoscope and the cannula to be frequently taken out and reinserted, which in itself lengthens the intervention times. Furthermore, even small variations in positioning of these two devices could lead to incorrect information and possibly to damage.

A liposuction cannula of the type initially defined is described in the U.S. Pat. No. 5,242,386. In this Patent, a liposuction cannula is provided in which, at the front end, a piezoelectric transducer is disposed which emits ultrasounds into the tissues surrounding the cannula. The analysis of the echoes received via the same transducer allows the depth of these tissues to be determined.

In this regard, it is observed that the piezoelectric transducers operate over a reduced frequency range, a fact which limits the depth of scanning and the resolution obtainable. In particular, the solution known from the said U.S. Patent does not allow blood and lymphatic vessels to be detected, and does not therefore allow any potential damage to be avoided.

The solution described in the said U.S. Patent furthermore does not allow video images to be obtained, also usable as a tool for training/information in order to enable surgical techniques to be further improved.

SUMMARY OF THE INVENTION

One aim of the present invention is to provide a liposuction cannula which allows the aforementioned drawbacks of the solutions according to the prior art to be overcome.

This and other goals are achieved according to the invention with a liposuction cannula of the type initially defined, characterized in that the aforementioned detector means comprise An imaging apparatus designed to supply first signals or data allowing the generation of a visual representation of the environment in close proximity to the front end of the tube of the cannula down to a first depth or distance, and second signals or data allowing the generation of a visual representation of the environment around the front end of the tube of the cannula down to a second depth or distance, greater than said first depth or distance.

The aforementioned first signals or data allow a "near-field" view to be formed, so as to allow the operator to view the tissues and the organic structures immediately adjacent to the end of the cannula, whereas the second signals or data provide an "in-depth" view that enables vital structures to be identified well in advance avoiding damaging them during the aspiration of the fat, thus improving the safety of the procedure.

In one embodiment, the imaging apparatus comprises first and second imaging devices for the generation of the near-field imaging signals or data and, respectively, of the in-depth imaging signals or data.

The first imaging device may for example be a scanning fibre endoscope (SFE), which allows coloured images to be generated and acquired that are conveniently displayed on a screen and that can advantageously be recorded.

SFE endoscopes designed for such a use are described for example in Seibel E J, Johnston R S, Melville C D, "A full-color scanning fiber endoscope", *Biomedical Optics* 2006, International Society for Optics and Photonics, 2006, Proc. SPIE 6083, Optical Fibers and Sensors for Medical Diagnostics and Treatment Applications VI, 608303, and also in Lee C M, Engelbrecht C J, Soper T D, Helmchen F, Seibel E J, "Scanning fiber endoscopy with highly flexible, 1-mm catheterscopes for wide-field, full-color imaging", J, Biophotonics, 2010; 3:385-407.

The second imaging device may for example be a device for optical coherence tomography (or OCT), of the type described for example in Kuo W C, Kim J, Shemonski N D, Chaney E J, Spillman D R Jr, Boppart S A, "Real-time three-dimensional optical coherence tomography image-guided core-needle biopsy system", Biomed Opt Express, 2012; 3:1149-61.

As an alternative, the second imaging device may be a capacitive micro-machined ultrasound transducer (or CMUT) device, for example of the type described in Stephens D, Truong U T, Nikoozadeh A, Oralkan O, Seo C H, Cannata J, Dentinger A, et al., "First In Vivo Use of a Capacitive Micromachined Ultrasound Transducer Array—Based Imaging and Ablation Catheter". J Ultrasound Med 2012; 31:247-256, and in Lorenser D, Yang X, Kirk R W, Quirk B C, McLaughlin A. Sampson D D, "Ultrathin side-viewing needle probe for optical coherence tomography", Opt. Lett. 2011; 36:3894-3896.

BRIEF DESCRIPTION OF THE FIGURES

Further features and advantages of the invention will become apparent from the detailed description that follows, presented purely by way of non-limiting example, with reference to the appended drawings, in which.

DESCRIPTION OF EMBODIMENTS

In the figures from 1 to 3, reference 1 is an overall indication of a liposuction cannula constructed in accordance with the present invention.

Such a cannula comprises a tube 2 made for example from a metal material, such as stainless steel or titanium brushed or coated with zirconium nitride, or else made of plastic material.

The tube 2 can have standard dimensions and, in particular, a length in the range for example between 7 and 30 cm.

The outer diameter of the tube 2 of the cannula according to the invention is for example 5-6 mm, in order to be able to define inside it at least one conduit capable of allowing the removal of the aspirated fatty tissue and the accommodation of the imaging means which will be described hereinbelow. The diameter of the tube 2 therefore depends, at least in part, on the dimensions of the imaging devices used and it is predictable that the continual improvements in such devices and in the corresponding technologies is going to allow the implementation of even thinner cannulae.

A handle 3, for example made of plastic material, is attached to one end of the tube 2. In a manner known per se, at least one passage for the evacuation of the aspirated fatty material is formed in this handle, in addition to at least one other passage for the electrical cables and/or the optical fibres connected to the imaging devices contained in the tube 2.

At the distal end, opposite to the handle 3, the tube 2 forms a tip with a convex curved profile, composed, at least in part, of a calotte 4 of transparent material for the radiation used by the imaging devices.

Figure 3:
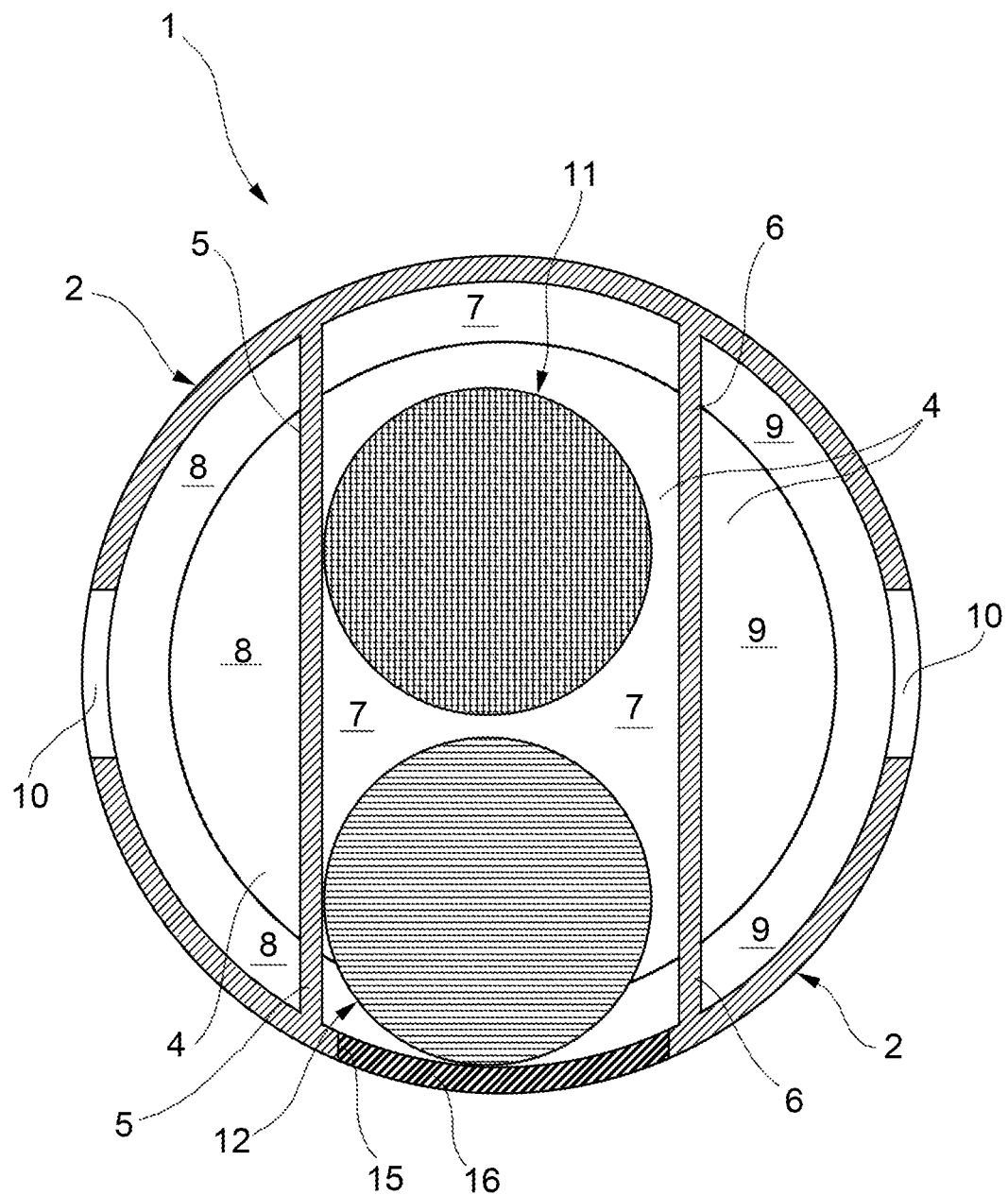
FIG. 3 shows, on an enlarged scale, the cross-section along the line III-III in FIG. 2.

With reference in particular to FIG. 3, the cavity defined inside the tube 2 is divided up, by means of two parallel longitudinal partition walls 5 and 6, into a central region or chamber 7 in which imaging devices and the connecting cables/fibres thereof are accommodated, and two lateral regions or chambers 8 and 9, acting as conduits for the flow of the aspirated fatty material.

The regions or chambers 7, 8 and 9 extend over the entire length of the tube 2. At the back end, or else near the handle 3, the chambers 8 and 9 may be connected, in a manner not shown, to a source of vacuum of the type known per se intended to carry out the aspiration.

The calotte 4 may be made of transparent Pyrex glass, or of a plastic material potentially coated with a thin metallization layer capable of acting, where necessary, as an electrode.

In proximity to the tip 4, in the side-wall portions of the tube 2 that cooperate to bound the regions or chambers 8 and 9, respective pluralities of aspiration apertures are formed, indicated by 10.

The number, the shape and the disposition of the apertures 10 illustrated in the figures are purely exemplary and non-limiting.

In proximity to the tip 4, in the region or chamber 7 of the tube 2, a first and a second imaging device are disposed, indicated by 11 and 12, respectively.

The imaging device 11 is capable of supplying signals or data able to allow a view of the environment immediately surrounding the inner end of the tube 2 of the cannula, down to a first depth or distance, for example 5-35 mm, so as to make available a display of the "near field" of operation.

The second imaging device 12 is, on the other hand, capable of supplying signals or data able to allow an in-depth view of the environment surrounding the front end of the tube 2 of the cannula, for example down to a distance equal to 5-6 cm, in order to, in particular, allow the operator to identify sufficiently in advance any potential blood or lymphatic vessels, and hence to be able to avoid damaging them.

Figure 2:
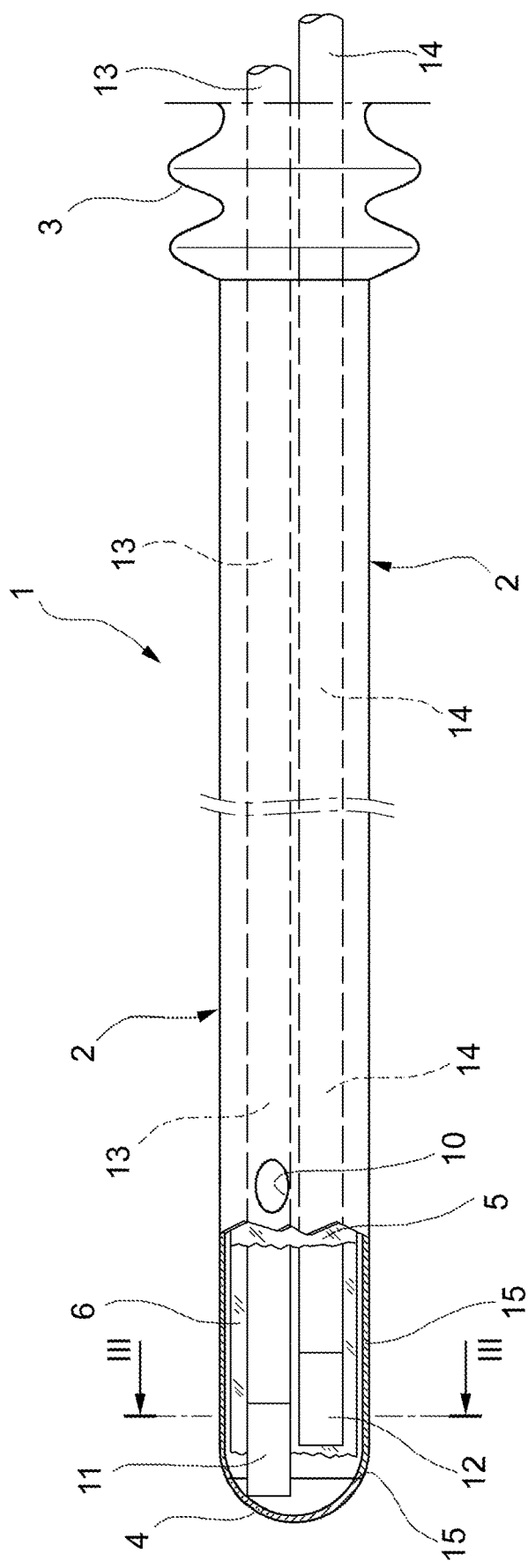
FIG. 2 is a partial side view, in partial cross-section, according to the arrow II in FIG. 1.

As has already previously been mentioned, the first imaging device 11 is for example a scanning fibre endoscope (SFE), shown schematically in FIGS. 2 and 3, equipped with a multipolar connecting cable 13 running within the central chamber 7 of the tube 2, and then through a corresponding central passage of the handle 3.

The second imaging device 12 can comprise a CMUT (Capacitive Micromachined Ultrasound Transducer) device of the types previously mentioned, which is associated with a respective cable 14 running longitudinally within the central chamber 7 of the tube 2, next to the cable 13 associated with the first imaging device 11.

The longitudinal partition walls 5 and 6 run over the entire length of the tube 2, as far as the calotte of the tip 4, in such a manner as to hermetically separate the central chamber 7 from the aspiration chambers 8 and 9, in order to guarantee sterile conditions within the latter.

Scanning fibre endoscopes are constructed with diameters of the order of a millimetre or a little more. Such an endoscope comprises a piezoelectric tube and a single-mode optical fibre, and it emits oscillations of light (red, green and blue light), and detects the back-scattered reflected light, containing information useful for forming the display of images.

In the cannula according to the invention, the transparent calotte or tip 4 allows the free passage of the light towards and from the tissues immediately adjacent to the distal portion of the tube 2, allowing the near field to be viewed, useful for guiding the operator in the use of the liposuction device.

With respect to other electronic cameras for medical use, the scanning fibre endoscope offers the advantage of an optimum clarity of the images, obtained with the employment of a microscopic camera, whereas the conventional electronic cameras, such as those using bunches of coherent optical fibres and which interpret the diffuse white light illumination, suffer significant loss of sharpness of the images when they are miniaturized. Such conventional electronic cameras do not allow, at the same time, both a high resolution and a wide field of view to be obtained, whereas scanning fibre endoscopes allow high quality images to be produced with an extensive field of view.

Since the scanning fibre endoscope uses a narrow-band RGB source of illumination, by means of the use of bio-markers, it is possible to perform an imaging of the tissues using fluorescence with a wide field of view.

As has been said hereinabove, the second imaging device 12 can comprise an OCT device, disposed in the tip of the tube 2 of the cannula, behind the calotte 4.

OCT devices emit light in the near-infrared, through a transparent window, using a laser.

OCT probes can implement a forward or side-on scanning (viewing). The devices with forward scanning offer the advantage of being more readily miniaturizable, and they are also produced as needle probes, with dimensions of the order of 0.25 mm.

OCT side-viewing probes allow images to be produced in 2D and 3D. The need to provide them with a micro-mirror renders their miniaturization more problematic. OCT side-viewing probes with diameters of the order of 0.40 mm have however been produced.

A catheter for OCT has furthermore been implemented, used for needle-biopsy, having an outer diameter of 0.9 mm. They are designed to produce two-dimensional radial images but, with the use of appropriate software, allow a 3D rendering to be produced.

OCT probes may also be implemented in such a manner as to enable fluorescent signals to be detected and to allow fluorescent 3D images to be generated that are able to supply more visual information around the structures of the tissues.

As previously said, the second imaging device 12 may be a CMUT device. Such devices, in contrast to the conventional devices using ultrasounds which employ piezoelectric technology, are not self-heating and are accordingly more suited to high-energy applications. CMUT devices can also be miniaturized without this being detrimental to the clarity of the images, and they operate with a much wider bandwidth compared with the conventional piezoelectric transducers.

CMUT devices can also be used to produce photoacoustic imaging (PAI) which combines optical imaging with acoustic imaging: short pulses from a laser briefly heat absorbing structures, such as blood vessels, and generate acoustic pressure waves which are detected via ultrasounds. These solutions have allowed the in-depth imaging to be significantly improved, guaranteeing clarity of images down to a depth of around 5 cm.

A CMUT device may be associated with the capacity to detect bio-markers, for example using indocyanine green fluorescence, in order to enable an optimal in-depth view of structures.

The recent technological developments allow CMUT devices to be used for an in-depth display of tissues and vulnerable structures, such as veins and lymphatic vessels, thus improving the safety of the liposuction procedure.

If the second imaging device 12 is of the side-viewing or side-scanning type, then, as is illustrated in the figures from 1 to 3, in the side wall of the tube 2, close to the tip or calotte 4, an aperture or window 15 is conveniently formed that is provided with a closing element 16 made of material transparent to the radiation used.

Figure 1:
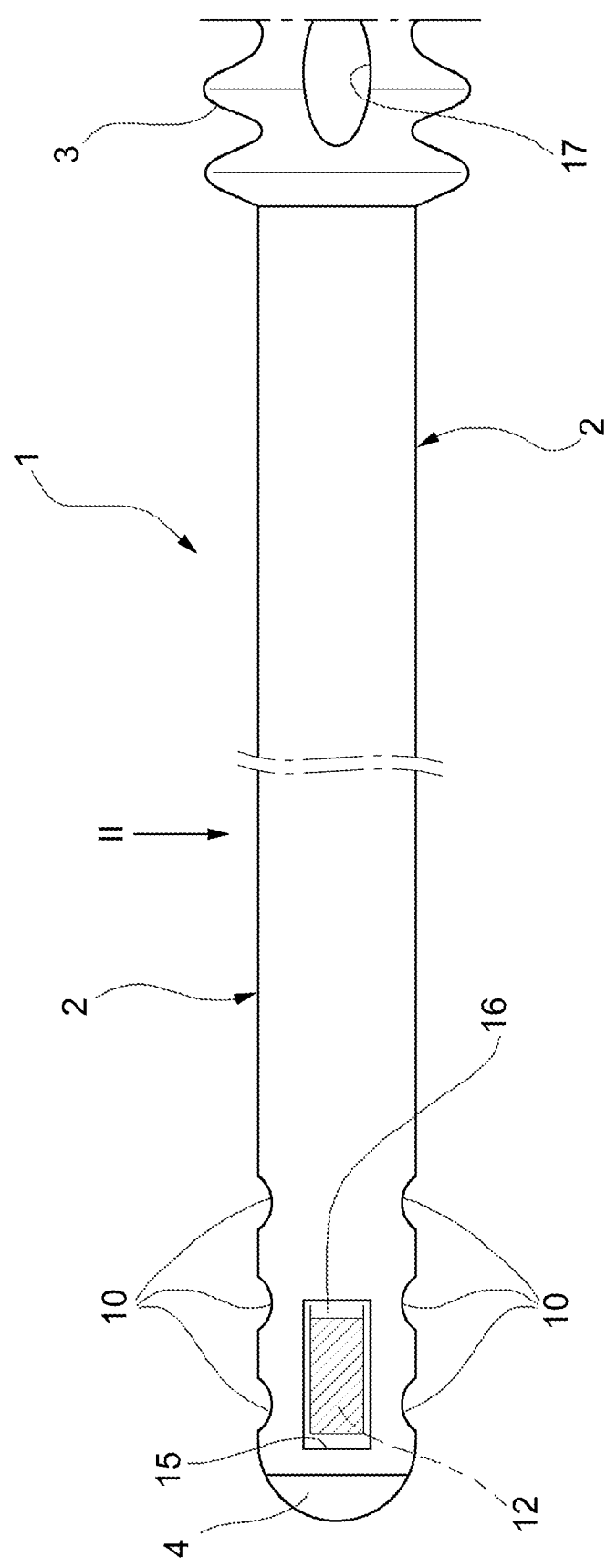
FIG. 1 is a partial side view of a liposuction cannula according to the present invention.

In this case, the handle 3 may conveniently comprise a reference, such as a hollow 17 (FIG. 1) in which the thumb of the hand of the operator is engaged, so that the latter therefore always has the orientation of the said window present.

Figure 4:
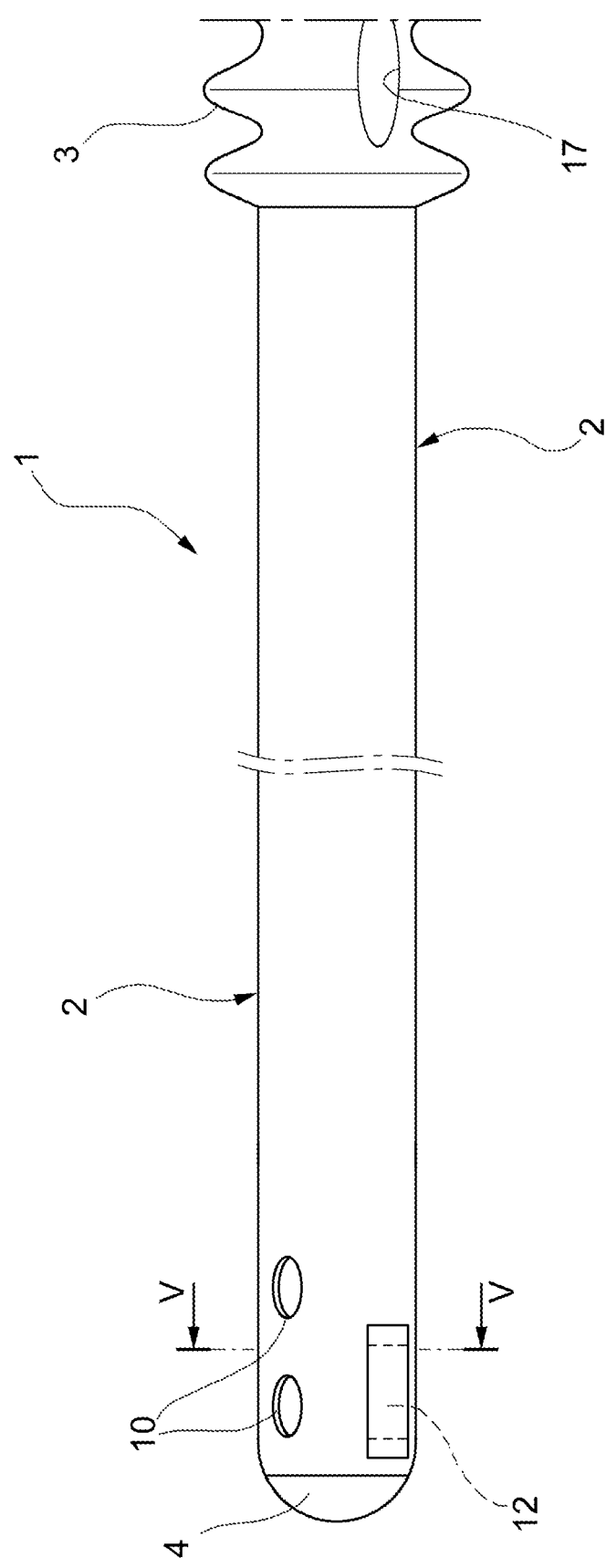
FIG. 4 is a partial side view of another embodiment of a liposuction cannula according to the present invention.
Figure 5:
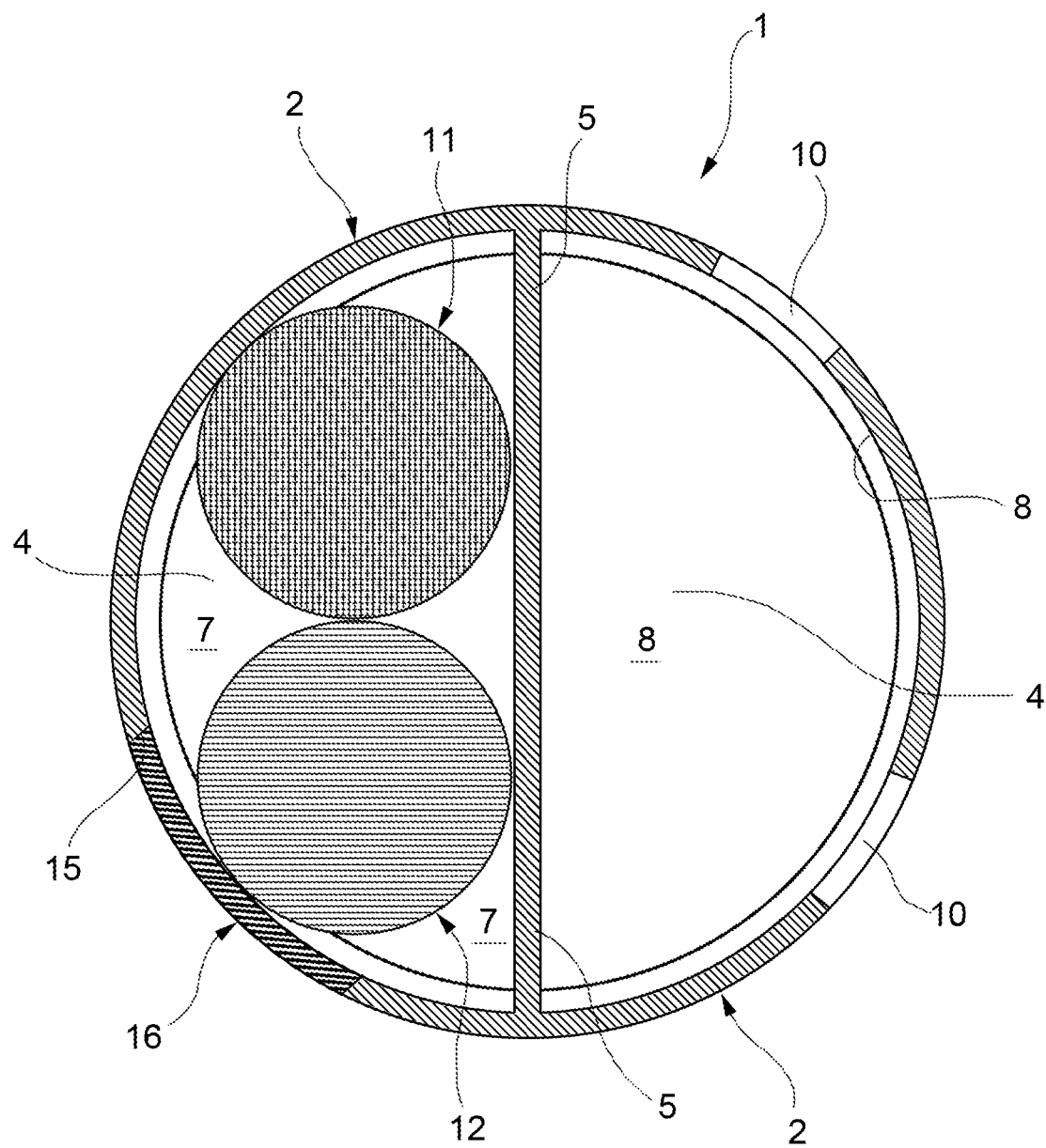
FIG. 5 shows, on an enlarged scale, the cross-section along the line V-V in FIG. 4.

FIGS. 4 and 5 show one variant embodiment. In these figures, to parts and elements that are equivalent or substantially corresponding to parts and elements already described, are again assigned the same reference numbers used previously.

In the variant according to FIGS. 4 and 5, the region internal to the tube 2 is divided up by a single longitudinal partition wall 5 into a first region or chamber 7, within which the imaging devices 11 and 12 and the connecting cables thereof are positioned, and a second region or chamber 8 acting as a conduit for the flow of the aspirated fatty material.

Also, in this case, the imaging devices 11 and 12 are conveniently of the type described above with reference to the embodiment according to the figures from 1 to 3. The portion of side wall of the tube 2 which is used to bound the chamber or region for aspiration 8 is also, in this case, provided with one or more apertures 10, through which the fatty material can be aspirated into the inside of the said region or chamber.

The solution according to FIGS. 4 and 5 may be implemented with a tube 2 having an outer diameter that is slightly smaller with respect to the embodiment according to the figures from 1 to 3.

A liposuction cannula according to the present invention allows near-field and in-depth video images of the tissues surrounding the distal end of the cannula to be supplied to the operating surgeon. Such images can be recorded, so as to be used as a tool for training/information.

The possibility for the operator to see the structures surrounding the cannula improves the safety of the procedure, minimizing the risk of damaging the adjacent structures. It is furthermore possible for the operator to perform an optimum removal of the fatty tissue, without compromising vulnerable structures, thus improving the efficacy of the procedure with respect to the equipment currently available. The current equipment, which does not allow viewing of the operating field, leads the operators to be cautious in the removal of the fatty tissue by default, in order to reduce the risks of damaging the adjacent structures, sometimes leaving a quantity of tissue in situ that could/should be removed.

It does of course go without saying that the principle of the invention, the embodiments and their details of implementation will be able to be widely varied with respect to what has been described and illustrated purely by way of non-limiting example, without however straying from the scope of the invention as defined in the appended claims.

The invention claimed is:

1. Liposuction cannula, comprising:
   a tube with a front end at which there is provided at least one suction opening, and with a back end intended to be connected to a source of vacuum; in the tube there being defined at least one longitudinal flow conduit for an aspirated material; and
   detector means arranged at the front end of said tube and capable of supplying in use signals containing information useful for an operator using the cannula;
   wherein said detector means comprise an imaging apparatus capable of supplying first signals or data allowing generation of a visual representation of an environment in proximity to the front end of the tube of the cannula down to a first depth or distance, and second signals or data allowing the generation of a visual representation of the environment around the front end of the tube of the cannula down to a second depth or distance, greater than the said first depth or distance,
   wherein said tube defines a cavity which, by at least one longitudinal partition wall extending from the front end to the back end thereof, is divided into at least two regions or chambers hermetically isolated from one another, in one of which there are accommodated a first image device and a second imaging device and connection cables thereof, and at least one other of which forms said longitudinal flow conduit for the aspirated material.

2. Liposuction cannula according to claim 1, wherein said imaging apparatus comprises said first imaging device capable of producing video signals or data for displaying the environment in proximity to the front end of said tube.

3. Liposuction cannula according to claim 1, wherein said imaging apparatus comprises said second imaging device capable of producing signals or data usable for displaying tissues in depth around the front end of said tube.

4. Liposuction cannula according to claim 2, wherein the first imaging device is a scanning fibre endoscope (SFE).

5. Liposuction cannula according to claim 3, wherein the second imaging device is an OCT device or a CMUT device.

6. Liposuction cannula according to claim 1, wherein an internal cavity of said tube is divided by two longitudinal partition walls into a central region or chamber in which the said imaging devices are accommodated with their connection cables, and two lateral regions or chambers acting as flow conduits for the aspirated material.

7. Liposuction cannula according to claim 1, wherein an internal cavity of said tube is divided, by a single longitudinal partition wall, into a first region or chamber in which said imaging devices and the connection cables thereof are accommodated, and a second chamber acting as a flow conduit for the aspirated material.

8. Liposuction cannula according to claim 2, wherein a distal portion of said tube has an end part or tip of a material transparent to radiation emitted and/or received by said imaging devices.

* * * * *